United States Patent [19]

Klein et al.

[11] Patent Number: 5,079,143
[45] Date of Patent: Jan. 7, 1992

[54] METHOD OF INDENTIFYING COMPOUNDS USEFUL AS ANTIPARASITIC DRUGS

[75] Inventors: Ronald D. Klein, Schoolcraft; Timothy G. Geary, Kalamazoo, both of Mich.

[73] Assignee: The Upjohn Company, Kalamazoo, Mich.

[21] Appl. No.: 517,633

[22] Filed: May 2, 1990

[51] Int. Cl.$^5$ .......................... C12Q 1/02; C12Q 1/68; C12N 1/20; C07H 15/12

[52] U.S. Cl. ................................ 435/29; 435/252.3; 435/252.33; 435/320.1; 435/6; 536/26; 536/27; 536/28; 536/29; 935/79

[58] Field of Search ................... 435/29, 257.3, 252.33, 435/320; 536/26, 27, 28

[56] References Cited

PUBLICATIONS

Hansen, E. J. and E. Juni, "Isolation of Mutants of *Escherichia coli* Lacking NAD- and NADP-Linked Malic Enzyme Activities", Biochem. Biophys. Res. Commun., 1975, 65(2)559–566.

Kemerer, V. F., et al., "Phosphofructokinase from *Escherichia coli*", Meth. Enzymol., 1975, 42:91–98.

Struhl, K., et al., "Functional Genetic Expression of Eukaryotic DNA in *Escherichia coli*", Proc. Natl. Acad. Sci. U.S.A., 1976, 73(5):1471–1475.

Ratzkin, B. and J. Carbon, "Functional Expression of Cloned Yeast DNA in *Escherichia coli*", Proc. Natl. Acad. Sci. U.S.A., 1977, 74(2):487–491.

Struhl, K. and R. W. Davis, "Production of a Functional Eukaryotic Enzyme in *Escherichia coli*: Cloning and Expression of the Yeast Structural Gene for Imidazole-Glycerolphosphate Dehydratase (his3)", Proc. Natl. Acad. Sci. U.S.A., 1977, 74(12):5255–5259.

Bach, M., et al., "Evidence for Transcriptional Regulation of Orotidine-5'-Phosphate Decarboxylase in Yeast by Hydridization of mRNA to the Yeast Structural Gene Cloned in *Escherichia coli*", Proc. Natl. Acad. Sci. U.S.A., 1979, 76(1):386–390.

Heinisch, J., "Isolation and Characterization of the Two Structural Genes Coding for Phosphofructokinase in Yeast", Mol. Gen. Genet., 1986, 202:75–82.

Rohrer, S. P., et al., "Purification and Characterization of Phosphoenolpyruvate Carboxykinase from the Parasitic Helminth *Ascaris suum*", J. Biol. Chem., 1986, 261(28):13049–13055.

Gehnrich, S. C., et al., "Liver (B-Type) Phosphofructokinase mRNA", J. Biol. Chem., 1988, 263(24):11755–11759.

*Primary Examiner*—Robert A. Wax
*Assistant Examiner*—Stephane W. Zitomer
*Attorney, Agent, or Firm*—Mark DeLuca

[57] ABSTRACT

A method for identifying compounds useful as antiparasitic drugs is disclosed. Deficient microorganisms are complemented with homologous metabolic enzyme genes. The metabolic enzyme is the drug target. In addition, recombinant DNA molecules comprising helminthic PFK and PEPCK genes are disclosed.

20 Claims, No Drawings

METHOD OF INDENTIFYING COMPOUNDS USEFUL AS ANTIPARASITIC DRUGS

FIELD OF THE INVENTION

The present invention relates to a method of screening compounds to identify agents useful as antiparasitic drugs.

BACKGROUND OF THE INVENTION

Current methods of identifying agents useful as antiparasitic drugs are inadequate and the use of molecular biology to this end has been limited. Nearly all molecular biology research done globally in parasites is devoted to antigen characterization and production with a goal of vaccine development. Discovery of drugs effective against many parasites is hampered by the inability to recover them in sufficient quantities to isolate proteins for study and screening. Many helminthic parasites grow poorly in convenient laboratory animals and are uniformly intractable to culture. Obtaining them from natural hosts, even in small quantities, is tedious and expensive.

Accordingly, using present methods, it is difficult to study parasites and screen compounds which may be useful as drugs against them. The absence of an effective method of finding antiparasitic drugs hinders efforts to successfully control or eradicate many diseases. The diseases or groups of diseases described generally as helminthiasis are due to infection of the animal with parasitic worms known as helminths. Helminthiasis and helminthosis are prevalent and may lead to serious economic problems in sheep, swine, cattle, goats, dogs, cats, horses, poultry and man. Among the helminths, the groups of worms known as nematodes, trematodes and cestodes cause widespread and often times serious infections in various species of animals including man. The most common genera of nematodes, trematodes, and cestodes infecting the animals referred to above are Dictyocaulus, Haemonchus, Trichostrongylus, Ostertagia, Nematodirus, Cooperia. Bunostomum, Oesophagostomum, Chabertia, Strongyloides, Trichuris, Fasciola, Diorocoelium, Enterobius, Ascaris, Toxascaris, Toxocara, Ascaridia, Capillaria, Hererakis, Ancylostoma, Uncinaria, Onchocerca, Taenia, Moniezia, Diplylidium, Mecastrongylus, Macracanthorhynchus, Hyostrongylus, and Strongylus. Some of these genera attack primarily the intestinal tract while others inhabit the stomach, lungs, liver and subcutaneous tissues. The parasitic infections causing helminthiasis and helminthosis lead to anemia, malnutrition, weakness, weight loss, unthriftiness, severe damage to the gastro-intestinal tract wall and, if left to run their course, may result in death of the infected animals Gastrointestinal nematodes, such as *Haemonchus contortus*, are important pathogens of sheep and cattle. These species are representative of a large number of economically significant ruminant parasites. These parasites are examples of those which present the above described problems in drug discovery.

One characteristic shared by many helminthic parasites is their dependence on a single pathway for energy generation. For intestinal parasites, glucose is an essential fuel. Pathways for energy generation in parasitic helminths differ from those in mammals and have long been proposed as targets for anthelmintic discovery. Nematodes which parasitize the gastro-intestinal tract are thought to be completely dependent upon the oxidation of glucose for the generation of energy. Gastrointestinal parasites are incapable of using amino acids or fatty acids as energy sources.

The present invention provides a new method of screening compounds in order to identify agents useful as antiparasitic drugs. The present invention provides an alternative to use of parasites as subjects to study and as sources of proteins. Thus, it is not necessary to collect large quantities of parasites, to grow them in vitro and to use them with convenient laboratory animals to study the parasites and screen for antiparasitic compounds.

The present invention provides a method of screening compounds by maintaining a target protein in a controlled biological system such that the effects on the target protein by the compound being screened can be easily observed. According to the present invention, it is possible to express specific parasite proteins in biological systems which will allow high volume screening for novel compounds with specific mechanisms of action. Furthermore, according to the present invention, the action of a compound on a target protein can be observed independent of other factors since the target protein is a metabolic pathway component which can be circumvented in control tests by addition of a substance capable of being metabolized by subsequent pathway components.

Potential drug targets include metabolic enzymes known to be the site of action of available antiparasitic drugs as well as those which, based on an understanding of parasite physiology and biochemistry, represent novel mechanisms of actions for selective chemotherapeutic intervention. Leads that differentiate between host and parasite on a mechanistic basis provide the most likely candidates for successful development. Through the identification characterization and cloning of potential drug targets and their expression in an appropriate system for the production of material for biochemical study and for the development of high volume mechanistic screens the difficulties associated with screening agents in parasite organism systems are avoided. Cloning important enzymes and structural proteins into systems permits high volume screening of target parasite species which are highly intractable to culture in vitro, and whose acquisition on a regular basis is expensive and difficult. Furthermore, in contrast to other chemotherapeutic targets, very little is known about host-pathogen differences, other than pharmacological, for parasitic organisms. A critical axiom of experimental chemotherapy is that exploitation of such differences is the key to successful treatment.

INFORMATION DISCLOSURE

Hansen. E. J. and E. Juni, Biochem. Biophys. Res. Commun. 65(2):559-566, 1975. refer to the isolation of mutants of *E. coli* lacking NAD- and NADP-linked malic enzyme activities. Chemical mutagenesis of a strain of *E. coli* lacking PEPCK activity yielded a mutant which lacks NAD-linked malic enzyme activity. A revertant of a double mutant was isolated which possesses NADP-linked malic enzyme activity. Mutagenesis of the revertant mutant yielded an *E. coli* strain which lacks NADP-linked malic enzyme activity, PEPCK activity and NAD-linked malic enzyme activities.

Kemerer, V. F. et al., Meth. Enzymol. 42:91-98, 1975, discloses the purification of PFK from *E. coli*.

Struhl, K. et al., Proc. Natl. Acad. Sci USA 73(5):1471–1475, 1976, refers to functional genetic expression of eukaryotic DNA in *E. coli*. A segment of DNA from eukaryotic *Saccharomyces cerevisiae* is reported as a viable molecular hybrid of bacteriophage λ DNA which, when integrated into the chromosome of *E. coli* histidine auxotrophs, allows the auxotrophic bacterium to grow in the absence of histidine. Expression of the eukaryotic DNA complemented the auxotrophic bacterium by providing a homologous functional enzyme lacking from the auxotrophic bacteria.

Ratzkin, B. and J. Carbon. Proc. Natl. Acad. Sci. USA 74(2):487–491, 1977, refer to the functional expression of cloned yeast DNA in *E coli*. Hybrid circular DNA's were constructed from *E. coli* plasmids and yeast DNA. The hybrid circular DNA's were used to transform auxotrophic bacteria Several of the hybrids complemented various E. coli auxotrophs.

Struhl, K. and R. W. Davis, Proc. Natl. Acad. Sci. USA 74(12): 255–5259, 1977, disclose a cloned segment of yeast DNA containing the structural gene for imidazoleglyerolphosphate dehydratase (D-erythro-imidazoleglycerolphosphate hydro-lase, EC 4.2.1.19) is transcribed and translated in *E. coli* with sufficient fidelity to produce functional enzyme.

Bach, M. et al., Proc. Natl. Acad. Sci. USA 76(1):386–390, 1979, disclose that yeast DNA which complemented nonreverting mutants of *E. coli* can be regulated in the same way that the yeast DNA expression is regulated in yeast.

Heinisch, J., Mol. Gen. Genet. 202:75–82, 1986, refers to the isolation and characterization of two structural genes coding for PFK in yeast. PFK double mutant yeast were transformed with yeast DNA to restore PFK function.

Rohrer. S. P. et al., J. Biol. Chem. 261(28):13049–13055, 1986 disclose the purification and characterization of PEPCK from parasitic helmintic *Ascaris suum*.

Gehnrich, S. C. et al., J. Biol. Chem. 263(24):11755–11759, 1988. disclose the cloning structure and expression of mouse liver B-type PFK mRNA. Characterization and sequence analysis of a cDNA clone corresponding to 2708 nucleotides of liver PFK mRNA is disclosed.

SUMMARY OF THE INVENTION

The present invention relates to a method of identifying compounds useful as antiparasitic drugs comprising the steps of exposing target gene-complemented microorganisms to compounds being investigated. The microorganisms used are originally deficient; that is, they are incapable of growing on a particular carbon source due to a defect in a gene for the requisite metabolic enzyme. The deficient microorganisms have been complemented with a homologous gene derived from the parasite species, rendering them capable of metabolizing the carbon source in the selection media. A second group of target gene-complemented microorganisms is also exposed to the compound being investigated. In addition a supplemental carbon source which bypasses the targeted metabolic enzyme in the metabolic pathway is added to the media of the second group. Accordingly, if the compound being tested interferes with the functioning of the target enzyme, it can be detected by observing the viability of the supplemented population and the death of the unsupplemented population.

Additionally, the present invention relates to recombinant DNA molecules comprising genes encoding target enzymes including *Haemonchus contortus* genes encoding phosphofructokinase (PFK), phosphoenolpyruvate carboxylkinase (PEPCK), and malic enzyme (ME). Furthermore, the present invention relates to expression vectors and transformed host cells comprising recombinant DNA molecules encoding parasite genes.

DETAILED DESCRIPTION OF THE INVENTION

The present invention provides a method for identifying compounds useful as antiparasitic drugs. The compounds identified by the present method will be useful as antiparasitic drugs which interfere with an essential metabolic enzyme of a metabolic pathway which the target parasite relies upon an order to convert a carbon source into energy An antiparasitic drug according to the present invention will be lethal to a parasite by preventing the parasite from metabolizing the carbon source.

Metabolic pathways are well known and extensively studied. An example of a metabolic pathway is that used to convert a carbon source into a usable energy source. This is done by a series of enzyme catalyzed reactions. Each enzyme is encoded by a different gene. Many metabolic pathways are common among organisms with each organism having a closely related homologous set of enzymes serving homologous functions in the series of reactions.

According to the present invention, a gene is isolated which encodes a metabolic pathway enzyme of a parasite which relies on such a pathway for survival. This gene is a target gene. As used herein "target gene" means a parasite-derived gene which encodes a metabolic enzyme that is essential in the metabolic pathway of a carbon source which the parasite relies upon for survival. As used herein, "target enzyme" refers to the metabolic enzyme encoded by a target gene.

The target gene is inserted into a microorganism that is deficient in the enzyme homologous to the target enzyme. As used herein, a "deficient microorganism" is a microorganism which is lacking a functioning metabolic enzyme necessary in a metabolic pathway. A deficient microorganism is incapable of growing on a selection media which contains only carbon source molecules that require the non-functioning metabolic pathway. The term "selection media" as used herein refers to media in which the only carbon source material contained therein cannot be used by deficient microorganism because of a non-functioning metabolic pathway due to a non-functioning or absent metabolic enzyme.

When the target gene is inserted into a deficient microorganism which is deficient due to the lack of a functioning metabolic enzyme homologous to the target enzyme, expression of the target gene provides the deficient microorganism with the functioning metabolic enzyme. The homologous metabolic enzyme performs the catalytic function in the metabolic pathway and thereby confers to the deficient microorganism the ability to live on selection media. The process of replacing a missing or non-functioning gene of a deficient microorganism with a functioning homologous gene in order to restore the deficient microorganism's ability to survive on selection media is called "complementation". As used herein, a "target gene-complemented microorganism" means a previously deficient microorganism which has been conferred the ability to live on selection media by introduction of a functioning homologous gene which is a target gene.

The isolation of the target gene and complementation of the deficient microorganism can be performed as a single step. Deficient microorganisms are transformed with total cDNA derived from the parasite species. Selection of target gene-complemented microorganisms may be performed by growing all cDNA transformed deficient microorganisms on selection media. Deficient microorganisms transformed with the target gene cDNA are complemented; only the complemented microorganisms will survive.

In the method of the present invention, target gene-complemented microorganisms growing on selection media are exposed to chemical compounds in order to determine whether the presence of the compounds can interfere with the functioning of the target enzyme. To determine this, two groups of target gene-complemented microorganisms growing on selection media are exposed to a compound; one is the test group and one is the control. In the control, a carbon source which bypasses the metabolic enzyme that is encoded by the target gene is added as a media supplement to one group. That is, a carbon source is added which can be metabolized by the microorganism lacking the target enzyme. Survival of the control group and the death of the unsupplemented group indicates that the compound added acts upon the target enzyme or an enzyme operating in an earlier catalyzed reaction in the pathway. As used herein, "selection media supplemented with a permissive substrate" refers to addition of a carbon source to selection media which can be metabolized by a deficient microorganism and which is metabolized in the metabolic pathway in reactions subsequent to that which is catalyzed by the target enzyme. One example of a permissive substrate is the catalysis product of the target enzyme. The presence of such a catalysis product in selection media would allow microorganisms with non-functioning target enzymes to complete the metabolic pathway and therefore survive.

The action of a compound on a target enzyme may be determined by comparing the viability of the two populations. As used herein, "comparing viability" means evaluating the relative conditions of microorganisms wherein death or retarded or impaired growth indicate low viability as compared to normal vigorous growth. One way of quantifying viability is to measure uptake of amino acids by a cell. This can be done by adding a radiolabelled amino acid source to the selection media. The amount of labelled amino acid found in cells indicates the level of protein synthesis occurring in the cell and thus the viability of the cell.

By complementing the deficient microorganism, one can study its response to potential drugs in the presence of a single carbon source which must be metabolized by the target enzyme versus a single carbon source which does not require the target enzyme. Agents which inhibit the growth and/or survival of the complemented microorganism when grown on the first carbon source, but not the second carbon source, are of interest as potential anthelminthics.

In another embodiment of the present invention, a second complementation may be performed to provide another control. A homologous parasite host gene, e.g., a homologous mammalian gene, may be used to complement a deficient microorganism. As used herein, "host gene-complemented microorganism" refers to a previously deficient microorganism which has been conferred with the ability to live on selection media by providing it with a functioning homologous gene which is derived from the host species upon which the parasite lives. The host gene-complemented microorganism is useful as a control because a compound that is shown to act on the target enzyme can be screened to determine whether it acts on the homologous enzyme of the host species. A compound that interferes with the activity of the target enzyme but not the activity of the host species homologous enzyme indicates potential safety of an antiparasitic drug comprising the compound.

The method of the present invention is useful in screening agents which are useful as drugs against nematodes. The present invention is useful in identifying antiparasitic drugs against many parasites including Dictyocaulus, Haemonchus, Trichostrongylus, Ostertagia, Nematodirus, Cooperia. Bunostomum, Oesophagostomum. Chabertia, Strongyloides, Trichuris, Fasciola, Dicrocoelium, Enterobius, Ascaris, Toxascaris, Toxocara, Ascaridia, Capillaria, Hererakis, Ancylostoma, Uncinaria, Onchocerca, Taenia, Moniezia, Dipylidium, Metastrongylus, Macracanthorhynchus, Hyostrongylus, and Strongylus.

The method of the present invention may be practiced using a variety of microorganism which can be complemented including E. coli and yeast.

The method of the present invention may use as a target enzyme many metabolic enzymes including phosphofructokinase (PFK), Phosphoenolpyruvate carboxykinase (PEPCK), and malic enzyme (ME).

Example 1

Method for Screening Compounds Useful as Antiparasitic Drugs Using *Haemonchus contortus* PFK in Deficient *E. coli*

Phosphofructokinase (PFK), the key regulatory enzyme in glycolysis, has been cloned from the pathogenic parasitic nematode *Haemonchus contortus* by complementation in *E. coli*. An *E. coli* strain deleted for both PFK loci (strain DF 1020) was transformed with *H. contortus* cDNA from a lambdaZAP II library. Two out of $8 \times 10^7$ transformants were able to grow on minimal medium with mannitol as the only energy source. A plasmid, pPFK, isolated from the transformants conferred the ability to grow on mannitol, sorbitol and mannose (the PFK phenotype). The plasmid, pPFK. was shown to contain a 2.7 kb insert associated with the PFK phenotype. The complemented cells contained PFK enzyme activity absent in the double mutant, at levels comparable to wild type *E. coli*. Sequence analysis of the 2.7 kb insert showed an open reading frame that encodes a 789 amino acid protein with very high similarity to mammalian PFKs. The active site around Asp 182 is completely conserved from mammals to nematodes. A putative phosphorylation site is located near the amino terminus. A strategy to use the E. coli complemented with pPFK in a nutrient-dependent viability assay as a high volume, mechanistic screen for novel PFK inhibitors is described.

Pathways for energy generation in parasitic helminths differ from those in mammals and have long been proposed as targets for anthelmintic drug discovery. Nematodes which parasitize the gastro-intestinal tract are thought to be completely dependent upon the oxidation of glucose for the generation of energy. These parasites also share an anaerobic mitochondrial pathway for energy production which results in the excretion of succinate and other fatty acids. Some, including *H. contortus*, are also capable of oxidative metabolism, while others, including the-best-studied parasitic nematode, *Ascaris suum*, are not. In any case, gastrointestinal parasites are incapable of using amino acids or fatty acids as energy sources.

Several enzymes in parasite energy metabolism appear to be targets for selective inhibition. Phosphofructokinase (PFK; ATP: D-fructose-6-phosphate 1-phosphotransferase, EC 2.7.1.11), is a key regulatory enzyme in glycolysis. The enzyme from *A. suum* and other nematodes is, like mammalian PFK, inhibited by ATP and stimulated by several cofactors, including AMP and hexosebisphosphate. Phosphorylation of PFK occurs in mammals and nematodes, but the nematode enzyme is different in that phosphorylation greatly enhances activity. In mammals, phosphorylation of PFK has variable effects, ranging from inhibition to mild stimulation. Based on this and other criteria, the enzyme from a variety of parasitic helminths is biochemically distinct from that of mammals.

Pharmacological data are available to support the argument that helminth PFK represents a selective drug target. Trivalent antimonials, especially stibophen, are effective but toxic anthelmintics. Antimonial drugs such as stibophen are known to act by selectively inhibiting worm PFK. Considerable evidence exists to suggest that these drugs inhibit PFK from nematodes, cestodes and trematodes 80-100 times more potently than mammalian PFK, and that lethal effects in parasites are associated with the inhibition of PFK. However, these compounds are still quite toxic to the host and have been completely supplanted by more modern drugs. Nonetheless, their broad spectrum of activity and known mechanism encourage a search for novel compounds which specifically inhibit nematode PFK. Isolation of pPFK:

Immature (21-day infections) *H. contortus* adults obtained from the abomasum of experimentally infected sheep were used for mRNA isolation. Both genders were used. Immature organisms were selected to avoid the preponderance of messages for egg and sperm production anticipated from sexually competent adults. The mRNA was isolated by guanidinium isothiocyanate (Sigma Chemical Co., St. Louis, Mo.) extraction of 2.44 g worms frozen and crushed in liquid nitrogen. Following CsCl centrifugation and polyA selection on oligo (dT) cellulose (Pharmacia), a cDNA library was constructed by Stratagene, Inc. (LA Jolla, Calif.) in lambdaZAP II. The titer of the amplified library was $5 \times 10^9$ pfu/ml, with insert size ranging from 500 bp to 10 kb and an insert frequency of approximately 95% as determined by the manufacturer.

Ten separate excision reactions with the *H. contortus* lambdaZAP IIc DNA library were done to achieve complete representation of the library. Each excision reaction was carried out essentially as described. *E. coli* XL-1 Blue (0.2 ml of $OD_{550}=1$ grown in 2X YT) was infected with 0.2 mls of the cDNA library ($2 \times 10^9$ pfu's/ml) and 1μl of R408 helper phage ($7 \times 10^{10}$ pfu's/ml). The infected cells were incubated at 37° C. for 15 minutes, added to 5 ml 2X YT and shaken at 37° C. for 2 hours. The resulting lysate was heated at 70° C. for 20 minutes and stored at 4° C. 0.2 ml of each "excision pool" was then used to infect 0.5 ml of E1628 ($OD_{550}=1$) in 2X YT at 37° C. for 15 minutes. The infected cells from each pool were then centrifuged, washed with 1X M9 salts and plated onto a 150 mm selection plate (M63-mannitol-proline-ampicillin) and incubated at 37° C. Aliquots from two of the samples were titered on AB2-ampicillin plates to determine the efficiency of excision and infection reactions. Each pool typically resulted in $1.5 \times 10^6$ ampicillin transductants. Colonies growing on the mannitol selection plates were purified on the same medium.

The phage cloning vector lambdaZAP II has the unique property of allowing for the in vivo excision of a plasmid ("phagemid") containing the recombinant DNA insert of interest, a Col El origin for plasmid replication, and an fl bacteriophage origin of replication for positive strand synthesis. These phagemids can then be introduced into the desired *E. coli* recipient by infection, where they will replicate via the plasmid origin of DNA replication and confer ampicillin resistance to the cell. If one of these particles contains a cDNA insert that confers a complementing phenotype on a suitable *E. coli* host, that plasmid can be isolated from the library.

*E. coli* strain DF1020 (F-, pro82, supE44, -, pfkB201, endA1, recA56, (rha-pfkA)200, thi-1, hsdR17) was obtained from the *E. coli* Genetic Stock Center Yale University, New Haven, Conn. (CGSC#6194). *E. coli* strain E1607 is a derivative of H3.5 (K37 PEPS-, PEPCK-, containing an F' that carries LACIq and chloramphenicol resistance. E1628 is DF1020 containing the F' from E1607 and is described below. M9 and M63 based minimal media were used as indicated. Succinate, mannitol, mannose, sorbitol, glycerol and glucose were used at 0.4% final concentration and proline was at 0.023%. Ampicillin, chloramphenicol and IPTG were used at 50 μg/ml, 20 μg/ml and 1 mM, respectively. For growth curves, cells were grown overnight in the specified medium at 37° C., subcultured into fresh medium the next day (1;100 dilution) and the density of the culture monitored by $OD_{550}$. Doubling times were calculated as described.

Cells were grown in LB media to $OD_{550}=0.5$; donor and recipient cells were mixed in an equal ratio and incubated for 2 hours with gentle shaking at 37° C. This mating mixture was centrifuged, washed in 1X M9 salts, plated onto selective plates and incubated at 37° C.

*E. coli* has two genes coding for PFK activities, PFKA and PFKB. A mutant deleted for both of these (DFl020) is unable to utilize any sugar entering glycolysis above fructose 6-phosphate. The rationale for isolating the *H. contortus* PFK gene was based on the idea that this PFK would complement *E. coli* DF1020 for growth on the six carbon sugar mannitol. Moreover, any such complementing activity should also allow for DFl020 to grow on mannose or sorbitol. Since the transducing particles generated from the lambdaZAP II library require the presence of an F' in the recipient cell, an F' was first introduced from E1607 into DF1020 as follows The donor strain, *E. coli* E1607 cannot grow on 4-carbon dicarboxylic acids and contains an F' carrying chloramphenicol resistance and lacIq whereas the recipient, DF1020, is chloramphenicol sensitive and can utilize 4-carbon dicarboxylic acids as a sole carbon and energy source. The strains were mated and transconjugants selected on M9 plates with succinate, proline and chloramphenicol. One of these transductants, E1628, was purified and found to be unable to grow on M9 plates, supplemented with mannitol and proline and used below.

Ten aliquots of the lambdaZAP II-H. contortus cDNA library were used to generate transducing particles containing the excised cDNA phagemids. These phagemids were introduced into E1628. Two of the aliquots were used to determine the number of ampicillin resistant transductants and the rest were spread onto M63 plates supplemented with mannitol, proline, chloramphenicol, ampicillin and IPTG. Two pools, 3 and 7, gave $4\times 10^6$ and $2\times 10^6$ transductants, respectively. A value of $3\times 10^6$ transductants per pool as an average gives a total of $3\times 10^7$ cDNA clones screened for PFK complementing activity using 10 pools. After incubation at 37° C. for 3-4 days two colonies appeared on the selection plates. These colonies were purified on identical media and plasmids isolated from each were used to retransform E1628. A transformant from one of these plasmids, E1688, grew on mannitol minimal media. E1688 contained a plasmid isolated from the lambdaZAP II cDNA library that conferred upon E1628 the ability to utilize mannitol as a carbon and energy source. E1688 also grew on minimal media containing sorbitol or mannose whereas E1628 did not, a phenotype that would be expected if the cDNA coded for a PFK activity and not some other enzyme that could shuttle mannitol into glycolysis by another mechanism. The plasmid from E1688, called pPFK, was also introduced by transformation into DF1020 generating cell line E1698 and found to confer the same growth phenotype on the 6-carbon sugars.

Sequence of the cDNA.

The plasmid pPFK was shown to contain a 2.7 kb insert. Large and small scale DNA isolations were carried out using the alkaline lysis method. Plasmid DNA for sequence analysis was prepared from 10 ml cultures using the alkaline lysis or PEG precipitation method as described. DNA restriction fragments were isolated by electroelution using a Gene Clean kit (BIO 10, La Jolla, Calif.) following the protocol provided by the manufacturer. Sheep genomic DNA was purchased from Clonetech, Inc. (Palo Alto, Calif.). DNA sequence analysis showed that the pPFK insert contained an open reading frame of 789 amino acids with approximately a 70% similarity to both the human muscle and mouse liver PFK. Further sequence analysis was conducted on pPFK, pPFK.A, pPFK.B, pPFK.C, pPFK.D and pPFK.E. The final assembly of the composite sequence was confirmed by sequencing through the boundaries of each of the sites defining these plasmids with pPFK as a template.

The gel entire DNA sequence and the predicted amino acid sequence presented in Chart 1.

DNA Hybridization Analysis

Southern hybridization analysis of *H. contortus* genomic DNA digested with various restriction enzymes and probed with the 1.5 kb BamHl/EcoRl fragment from the central portion of the cDNA clone was performed.

Approximately 5 μg of DNA was fractionated in 0.7% agarose gels as described and transferred to Gene Screen Plus (Dupont, Boston, Mass.). Isolated restriction fragments were labelled with 3,000 Ci/mmol $(\alpha)^{32}$P.dATP (Amersham Corp., Arlington Heights, IL) by random priming as described before.

Hybridization analysis using the 1.5 kb BamHl/EcoRl fragment as a probe resulted in two bands each for HindIII (9.6 and 1.5) and EcoRl (4.0 and 3.5) as expected for enzymes that cleave the insert once. An EcoRl/HindIII double digest produces three bands at 4.0, 1.8 and 1.5 kb, the latter corresponding to the expected internal fragment. An EcoRl/BamHI double digest produces three bands at 4.3, 3.5 and approximately 1.6 kb with the latter band corresponding to the expected internal fragment. Attempts to show hybridization to genomic digests of sheep DNA, even at low stringency, were not successful. These data confirm not only that the cDNA clone is from *H. contortus*, but suggest either the presence of small introns or their absence from the region extending from the BamHI site at 790 bp to the EcoRl site at 2221 bp.

Sequence Analysis

The plasmid pPFKA.1 contained a 2.7 kb cDNA insert cloned into the EcoRl site of the Bluescript SK vector. Fragments for subcloning were identified by restriction enzyme mapping. The following subclones were used: pPFK.A with a 2.1 kb EcoRl fragment which included the amino terminus of the cDNA; pPFK.B, with a 600 bp EcoRl fragment which included the carboxy terminus; pPFK.C, with a 1.4 kb Hind III fragment from the 5' half of the clone; pPFK.D, with a 1.3 kb Hind III fragment from the 3' half; and pPFK.E, with a 300 bp BamHI insert that contained part of the 5' region. The plasmid, Bluescript KS (Stratagene, Inc., La Jolla, Calif.), served as the vector for these constructions.

SK and KS primers were purchased from United States Biochemical Corp. (Cleveland, Ohio). Oligonucleotide primers for sequencing were synthesized on an ABI 380A or 380B DNA Synthesizer using the phosphoramidite triester coupling approach, dried in vacuo, then resuspended to a final absorbance of 1 at 260 nm and used without further purification to prime sequencing reactions as described below.

All DNA sequence analysis was by the dideoxy nucleotide chain termination method of Sanger et al. (1977) with double stranded plasmid DNA as the template using a Sequenase kit (United States Biochemical Corp., Cleveland, Ohio) as per the manufacturer's instructions. Primer annealing was as follows: 2 μg of double or single stranded DNA was denatured in 10 μl of 0.2M NaOH at room temperature for 5 minutes. Three pmol of primer and 3 μl of 3M sodium acetate were then added and the volume brought to 20 μl with water. 75 μl of ethanol was then added and the mixture placed on dry ice. After 5 minutes the mixture was centrifuged in a MTX-150 microcentrifuge (Tomy-Seiko, Tokyo, Japan) for 5 minutes, the ethanol was removed, the pellet carefully washed with 200 μl of 70% ice-cold ethanol and taken to dryness in a Savant Speed Vac Concentrator (Savant Instruments, Farmingdale, N.Y.). Two μl of 10x stock sequencing buffer and 8 μl of water were then added to the dried pellet and the labelling reaction performed.

20 cm or 33 cm×60 cm 6% acrylamide-7M urea sequencing gels (CBS Scientific Inc., Del Mar, CA) were used to obtain sequences starting typically from 20 to 30 bases from the priming site out to about 400 bases in a single loading. Similar results were also obtained using wedge-gradient gels with a spacer to wedge ratio of 1:4. in a single loading. Priming was with $\alpha(^{32}P$-)dATP (3000 Ci/mmole, Amersham Arlington Heights. IL). Gels were removed from the glass plates with 3 mm Whatman filter paper (Whatman Ltd., Madistone, England) and dried; a readable sequence could be obtained after a one hour exposure using Kodak XAR-plus film without intensifying screens.

Analysis of nucleotide sequences were performed using a VAX computer and DNA program package available from the University of Wisconsin Genetics Computer Group. DNA sequences were from GenBank (release 59.0); peptide sequences were generated using the DNA program package and protein sequence identities were assessed using the BESTFIT and GAP programs and FASTP algorithm. The nucleotide sequence is numbered with the first base 3' to the polylinker being designated "1 bp". The amino acid sequence is numbered with the first met being "1".

Screen Design

The screen is designed to identify agents (synthetic compounds or compounds in fermentation beers) which affect the growth of the complemented strain differentially when mannitol or glycerol is used as the sole carbon source. Agents which prevent growth on mannitol, but permit it on glycerol must inhibit the nematode PFK or E. coli aldolase or triosphosphate isomerase. Further characterization at the enzyme level will define the site of inhibition. Agents can then be tested on parasites and mammalian cells in culture and, if appropriate, on the purified mammalian enzyme.

Screening Protocol

E. coli 1698 (PFK+) is used to screen for inhibitors of PFK. Cells are grown and the assay conducted in sterile medium of the following composition (g/L): NaCl, 4.67; NH$_4$Cl, 1.07; Na$_2$SO$_4$, 0.426; MgC$_{12}$.6H$_2$O, 0.203; CaC$_{12}$.2H$_2$O, 0.029; KH$_2$PO$_4$, 3.0; K$_2$HPO$_4$, 7.0; ZnC$_{12}$, 0.27 mg. The medium is supplemented with caseamino acids. The latter is added aseptically to a final concentration of 5.0 g/L. Mannitol (4.0 g/L) or glycerol (2.0 g/L) are also added aseptically as carbon sources.

A loopful of the organism is inoculated into 100 ml of medium containing the appropriate carbon source. Each culture is incubated overnight at 37° C. with shaking (200 rpm) and is used as an inoculum for an overnight culture (inoculation rate, 5%). The culture is incubated overnight and is used to inoculate wells of a 96-well microtiter plate containing 50 μl fermentation beer extract or synthetic compound and the appropriate growth medium (100 μl). 25 μl of culture are added to each well such that the resulting OD at 570 nm is 0.1–0.2. The plates are incubated at 37° C. with shaking for two hours. At this time $^{14}$C-leucine (1.0 μCi/ml) is added to each well and incubation continued for another 2 hours. The final volume in the assay is 200 μl. Following this last incubation, the cells are harvested on a Skatron cell harvester and the filtermats counted with a LKB Beta Scintillation Counter.

Data are analyzed with respect to percent of inhibition of $^{14}$C-leucine cell associated counts in the wells which contain mannitol as compared to the wells which contain glycerol. For a tentative positive to be identified, inhibition of $^{14}$C-leucine uptake would be detected when E. coli 1698 (PFK+) grow on mannitol but not glycerol. This screening assay is based upon detecting some inhibitor of the enzyme PFK, by looking at protein synthesis dependent upon mannitol versus glycerol catabolism as measured by $^{14}$C-leucine uptake.

Example 2

Method for Screening Compounds Useful as Antiparasitic Drugs Using Haemonchus contortus PEPCK in Deficient E. coli Phosphoenolpyruvate carboxykinase (PEPCK) is another enzyme in energy metabolism of parasitic helminths which is a rational target for drug discovery. PEPCK in mammals functions primarily in gluconeogenesis, a process in which the products of glycolysis are reassembled into sugar for storage. In helminths, the enzyme is the major route for the introduction of the products of glycolysis (phosphoenolpyruvate) into substrates for mitochondrial metabolism (oxaloacetate). These different functions are explained by different kinetics observed for PEPCK purified from mammals vs. helminths. The inherent biochemical and functional differences confirm that PEPCK is a valid target for anthelmintic drugs.

PEPCK has been cloned from the parasitic nematode Haemonchus contortus by complementation in E. coli. An E. coli strain with mutations in PEPCK and the two malic enzyme loci (strain E1786) was transformed by electroporation with the H. contortus cDNA library described in Example 1. Complemented strains were selected by the ability to grow on minimal medium with malate as the only carbon source. One of the transformants contained a plasmid, p1786-27, which repeatedly conferred a mal +phenotype on E. coli strain E1786. This plasmid contains a 1.9 kb insert which hybridizes in Southern analyses to H. contortus but not sheep genomic DNA and bears 74.5% and 73.4% sequence similarity to Drosophila and chicken PEPCK, respectively. E. coli strain E1786 transformed with p1786-27 contains PEPCK enzymatic activity, while E1786 without p1786-27 does not. These data confirm that we have cloned PEPCK from a parasite helminth. A method to use the E. coli complemented with p1786-27 in a nutrient-dependent viability assay as a high volume, mechanism-based screen for novel PEPCK inhibitors, much like that in Example 1, is described.

Plasmids for electroporation were excised from the lambda ZAPII cDNA library as described in Example 1. E. coli strain E1786 (strain 1321 of Hansen and Juni, 1975; F', lac Iq. cam. PEPCK-, NAD+-ME-, NADP+-ME-) was obtained from Dr. Elliot Juni, Department of Microbiology, University of Michigan, Ann Arbor, Mich. 48104. E. coli strain E1786 (strain 1321) is available from the E. coli Genetic Stock Center, Yale University, New Haven, Conn. (CGSC #EJ1321). Media used were as described in Example 1, except that malate was used at 2% final concentration.

Electroporation was carried out with a Biorad Gene Pulser apparatus. E1786 cells were prepared for electroporation as per manufacturers instructions. An aliquot of cells was mixed with an aliquot of p1786-27 and placed on ice for 1 min. The mixture was transferred into a cuvette-electrode (1.9 cm) and pulsed once for 4.5–5 sec at a field strength of 12.5 kV/cm as per manufacturers instructions. The mixture was then added to 1 ml SOC medium (2% tryptone, 0.5% yeast extract, 10 mM NaCl, 25 mM KCl, 10 mM MgCl$_2$, 10 mM MgSO$_4$, 20 mM glucose) and shaken at 37° for 2–3 h. The cells were then plated onto M9 media containing 2% malate, 50 ug/ml ampicillin and 1% proline. These plates were incubated at 37° for 2–4 weeks or until colonies appeared.

A colony was purified on identical medium and a plasmid isolated from it used to transform E1786 as in Example 1. This plasmid, termed p1786-27, conferred the ability of E1786 to grow on malate.

Enzyme activity in bacterial supernatants obtained as described in Example 1 was measured by a spectrophotometric assay which detected the carboxylation of phosphoenolpyruvate to oxaloacetate by measuring the rate of formation of malate from oxaloacetate using malate dehydrogenase. E1786 had undetectable levels of PEPCK using this assay, while p1786-27 had 0.01 U/mg supernatant.

Growth curves (determined as in Example 1) for E1786 and E1786 transformed with p1786-27 were determined in M9 media containing 2% malate or pyruvate show that the two strains grow equally well in pyruvate. E1786 containing p1786-27 grows as well on malate as on pyruvate, but E1786 does not grow on malate.

Plasmid DNA for sequencing and Southern hybridization analysis was as described in Example 1. DNA sequence analysis showed that the p1786-27 insert contained an open reading frame of 613 amino acids with approximately 74% similarity to Drosophila and chicken PEPCK. The 1.9 kb insert obtained by restriction of p1786-27 was shown to hybridize to genomic DNA obtained from *H. contortus* but not sheep genomic DNA.

Screening Protocol for PEPCK Inhibitors

The screen is designed to identify agents (synthetic compounds or fermentation beers) which affect the growth of the complemented *E. coli* strain differentially when malate or pyruvate is used as the sole carbon source. Agents which prevent growth on malate but not pyruvate must inhibit the nematode PEPCK These agents can then be tested on parasites and mammalian cells in culture and, if necessary, in assays using the mammalian enzyme. The screen functions exactly as described for the PFK screen (Example 1) except that caseamino acids are omitted and the medium contains either pyruvate or malate (2.0 g/L) instead of mannitol or glycerol.

CHART 1

```
      CTCCGTCCGT TCTCACAACT ACCCCCCTTC CCCTTCGGTA CCCGCCCCTA
1     ----------+----------+----------+----------+----------+
      GAGGCAGGCA AGAGTGTTGA TGGGGGGAAG GGGAAGCCAT GGGCGGGGAT

ACCCGGCGTA ACTTACTTGG CTATTGTCTG ACTGTTCGTC CACATGCTTA
      ----------+----------+----------+----------+----------+ 100
      TGGGCCGCAT TGAATGAACC GATAACAGAC TGACAAGCAG GTGTACGAAT

GTACTCGCTA ATAATTATGG CTAATAATTA TGGCTAATCC ACATAATCCT
101   ----------+----------+----------+----------+----------+
      CATGAGCGAT TATTAATACC GATTATTAAT ACCGATTAGG TGTATTAGGA

CATCATGAGG TTGATGCCTT CCAAGACGAT AATATTATCC GCGATGAGGA
      ----------+----------+----------+----------+----------+ 200
      GTAGTACTCC AACTACGGAA GGTTCTGCTA TTATAATAGG CGCTACTCCT

TATGGAAGGA CAATCTGGGG CCGACGGCCA GGTCCCCTAC CCGACTTGCG
201   ----------+----------+----------+----------+----------+
      ATACCTTCCT GTTAGACCCC GGCTGCCGGT CCAGGGGATG GGCTGAACGC
      GCAATGAGCC TCAAAAGGAA TATACGTCGA CTGGACTTCCA TCGTGCCGAC
      ----------+----------+----------+----------+-----INAREA
      CGTTACTCGG AGTTTTCCTT ATATGCAGCT GACCTGAGGT AGCACGGCTG
      --+ M00  S   L   K   R   N   I   R   R   L   D   S   I   V   P   T
         1                  ++++++++++++++++++++++++++++++++++

AGCCGGACGA GAAGGTTCCG ACATTCAGTT CAACCTCTAT AAAGGCCGTG
301   ----------+----------+----------+----------+----------+
      TCGGCCTGCT CTTCCAAGGC TGTAAGTCAA GTTGGAGATA TTTCCGGCAC
       A   G   R   E   G   S   D   I   Q   F   N   L   Y   K   G   R   G

GAGTTGCAGT TTTCACATCT GGTGGTGACT CACAAGGAAT GAATGGCGCC
      ----------+----------+----------+----------+----------+ 400
      CTCAACGTCA AAAGTGTAGA CCACCACTGA GTGTTCCTTA CTTACCGCGG
       V   A   V   F   T   S   G   G   D   S   Q   G   M   N   G   A

GTGCATTCAG TCGTTCGTAT GGGTATTTAC CTCGGTTGTA AGGTGTGCTT
401   ----------+----------+----------+----------+----------+
      CACGTAAGTC AGCAAGCATA CCCATAAATG GAGCCAACAT TCCACACGAA
       V   H   S   V   V   R   M   G   I   Y   L   G   C   K   V   C   F
       50

TATCAATGAG GGATATCAAG GAATGGTTGA CGGTGGTGAT AACATTGTCG
      ----------+----------+----------+----------+----------+ 500
      ATAGTTACTC CCTATAGTTC CTTACCAACT GCCACCACTA TTGTAACAGC
       I   N   E   G   Y   Q   G   M   V   D   G   G   D   N   I   V   E

AAGCTAGCTG GAACTCGGGG TCCGACATCA TTCAAAAGGG AGGAACAATC
501   ----------+----------+----------+----------+----Y<<
      TTCGATCGAC CTTGAGCCCC AGGCTGTAGT AAGTTTTCCC TCCTTGTTAG
      -----A  S   W   N   S   G   S   D   I   I   Q   K   G   G   T   I
```

-continued

CHART 1

```
       ATCGGTTCAG CTAGATGTAC TGATTTGCGC CAACGAGAAG GCCGAATGAA
       ---------+----------+----------+----------+----------+  600
       TAGCCAAGTC GATCTACTAC ATG AAACGCG GTTGCTCTTC CGGCTTACTT
        I  G  S  A  R  C  C  D  L  R  Q  R  E  G  R  M  K
       100

GGCTGCGTAC AACCTCATTG AGAAAGGTAT CACCAATTTG GTGGTCATTG
   601 ---------+----------+----------+----------+----------+
       CCGACGCATG TTGGAGTAAC TCTTTCCATA GTGGTTAAAC CACCAGTAAC
         A  A  Y  N  L  I  E  K  G  I  T  N  L  V  V  I  G

GTGGTGATGG TTCACTCATA GGTGCAAATC AATTCCGAAA AGACTGGCCA
       ---------+----------+----------+----------+----------+  700
       CACCACTACC AAGTGAGTAT CCACGTTTAG TTAAGGCTTT TCTGACCGGT
          G  D  G  S  L  I  G  A  N  Q  F  R  K  D  W  P

GGGCTTGTCA AGGAACTGGT GGATACAAAG AAGATCACCC CAGAAGCTGC
   701 ---------+----------+----------+----------+----------+
       CCCGAACAGT TCCTTGACCA CCTATGTTTC TTCTAGTGGG GTCTTCGACG
         G  L  V  K  E  L  V  D  T  K  K  I  T  P  E  A  A
       150

CAAGAGTTAT CCCAATATAC AGATTGTTGG TCTCGTCGGA TCCATTGACA
                  ---------+----------+----------+----------+
                  GTTCTCAATA GGGTTATATG TCTAACAACC AGAGCAGCCT --+ 800
                   K  S  Y  P  N  I  Q  I  V  G  L A G V A  C T S N A R E A
                                                   +++++++++++++++ N
       ++++++↑+++
       ATGACTTCTG TGGTACCGAC ATGACCATCG GTACTGACAG CGCACTGCAA
   801 ---------+----------+----------+----------+----------+
       TACTGAAGAC ACCATGGCTG TACTGGTAGC CATGACTGTC GCGTGACGTT
         D  F  C  G  T  D  M  T  I  G  T  D  S  A  L  Q
       +++++++++++++++++++++++++++++++++++++++++++++++++

CGTATAATTG AGTCCATCGA TGCTGTAGTT GCCACAGCTC AAAGCCATCA
       ---------+----------+----------+----------+----------+  900
       GCATATTAAC TCAGGTAGCT ACGACATCAA CGGTGTCGAG TTTCGGTAGT
        R  I  I  E  S  I  D  A  V  V  A  T  A  Q  S  H  Q
       200 ++++

ACGTGCATTC GTGGTTGAGG TCATGGGTCG CCACTGCGGT TATCTTGCCC
   901 ---------+----------+----------+----------+----------+
       TGCACGTAAG CACCAACTCC AGTACCCAGC GGTGACGCCA ATAGAACGGG
          R  A  F  V  V  E  V  M  G  R  H  C  G  Y  L  A  L

TTGTTGCTGC TTTGGCATGT GAAGCTGATT TTTGCTTCAT CCCAGAATGG
       ---------+----------+----------+----------+----------+  1000
       AACAACGACG AAACCGTACA CTTCGACTAA AAACGAAGTA GGGTCTTACC
         V  A  A  L  A  C  E  A  D  F  C  F  I  P  E  W

CCTCCTCCAG TCAACTGGCG TGAAATTCTC TGCAAAAAGT TGCAGGAGAT
  1001 ---------+----------+----------+----------+----------+
       GGAGGAGGTC AGTTGACCGC ACTTTAAGAG ACGTTTTTCA ACGTCCTCTA
         P  P  P  V  N  W  R  E  I  L  C  K  K  L  Q  E  M
       250

GAGAGCTGAA GGTCAACGAC TGAACATCAT TGTCGTTGCT GAGGACGATG
       ---------+----------+----------+----------+----------+  1100
       CTCTCGACTT CCAGTTGCTG ACTTGTAGTA ACAGCAACGA CTCCTGCTAC
         R  A  E  G  Q  R  L  N  I  I  V  V  A  E  D  D  D

ATCGAGATGG CACTCCAATA TCGTCAGATC TCGTCAAAGA TGTCGTCGCT
  1101 ---------+----------+----------+----------+----------+
       TAGCTCTACC GTGAGGTTAT AGCAGTCTAG AGCAGTTTCT ACAGCAGCGA
          R  D  G  T  P  I  S  S  D  L  V  K  D  V  V  A

AAGACACTCA AATACGACAC AAGGGTGACC GTGCTTGGTC ATGTCCAACG
       ---------+----------+----------+----------+----------+  1200
       TTCTGTGAGT TTATGCTGTG TTCCCACTGG CACGAACCAG TACAGGTTGC
         K  T  L  K  Y  D  T  R  V  T  V  L  G  H  V  Q  R
       300

TGGAGGCTCA CCTTCAGCCT TTGATCGTCT CCTCGGTTGC AGAATGGGTG
  1201 ---------+----------+----------+----------+----------+
       ACCTCCGAGT GGAAGTCGGA AACTAGCAGA GGAGCCAACG TCTTACCCAC
          G  G  S  P  S  A  F  D  R  L  L  G  C  R  M  G  A
```

-continued

```
       CGGAGGCAGT ACTCGCTCTT ATGGAAATGA ACGAGGAATC CGAACCGTGC
       ---------+ ---------+ ---------+ ---------+ ---------+ 1300
       GCCTCCGTCA TGAGCGAGAA TACCTTTACT TGCTCCTTAG GCTTGGCACG
         E  A  V  L  A  L  M  E  M  N  E  E  S  E  P  C

GTCATTTCTA TCATGGTAAC CAGATGGTAC GTTCCGCTGA TGCAATGTGT
 1301  ---------+ ---------+ ---------+ ---------+ ---------+
       CAGTAAAGAT AGTACCATTG GTCTACCATG CAAGGCGACT ACGTTACACA
         V  I  S  I  M  V  T  R  W  Y  V  P  L  M  Q  C  V
       350

GGAGCGAACC AAAGCGGTAC AAAAGGCGAT GAGCGAGAAA GATTGGGAAC
       ---------+ ---------+ ---------+ ---------+ ---------+ 1400
       CCTCGCTTGG TTTCGCCATG TTTTCCGCTA CTCGCTCTTT CTAACCCTTG
         E  R  T  K  A  V  Q  K  A  M  S  E  K  D  W  E  L
```

```
1401  TCGCTGTCAAGTTACGTGGGCGAAGCTTCCAACGAAATCTGGAAACCTAC
        A  V  K  L  R  G  R  S  F  Q  R  N  L  E  T  Y

AAGTTACTAACAAAACTGCGTACAGTGGAAAAAGACAATCTTTCCGGTGG  1500
             K  L  L  T  K  L  R  T  V  E  K  D  N  L  S  G  G

1501  TCAGAACTTCAACGTTGCTGTCATGAATGTCGGCGCTCCTGCTGGAGGTA
        Q  N  F  N  V  A  V  M  N  V  G  A  P  A  G  G  M

TGAACGCAGCCGTTCGATCGTTTGTACGTATGGCCATTGTACCATCACTG  1600
                 N  A  A  V  R  S  F  V  R  M  A  I  V  P  S  L

1601  TACAGTTTACGGTATGAAGATTCCTTCGAAGGTCTCGCAAATGGAGCTTT
        Y  S  L  R  Y  E  D  S  F  E  G  L  A  N  G  A  F

TAAGAAATTCCAATGGGGAGATGTGACCAACTGGGTGATGCACGGCGGTT  1700
                K  K  F  Q  W  G  D  V  T  N  W  V  M  H  G  G  S

1701  CATTCCTTGGCACCCAAAAACAACTTCCCAATGAAAAGAACGTCCCACTG
        F  L  G  T  Q  K  Q  L  P  N  E  K  N  V  P  L

ATCGCAGAACAACTCAGAAAGCATAATATACAAGCGCTACTGCTTGTTGG  1800
                  I  A  E  Q  L  R  K  H  N  I  Q  A  L  L  L  V  G

1801  AGGATTGAGGCCTACCATTCCACTCTTATTCTGTCGAAGAATCGTGAAA
        G  F  E  A  Y  S  S  T  L  I  L  S  K  N  R  E  K

AATACCCCGAGTTCTGCATTCCGCTATGTGTCATACCATGTACCATCAGC  1900
                   Y  P  E  F  C  I  P  L  C  V  I  P  C  T  I  S

1901  AACAATGTACCAGGTACTTCGATATCCTTAGGCTCTGATACAGCTATCAA
        N  N  V  P  G  T  S  I  S  L  G  S  D  T  A  I  N

TGAGATCTGCACAATGATCGACAAAATTAAGCAGTCAGCTACGGGAACTA  2000
                   E  I  C  T  M  I  D  K  I  K  Q  S  A  T  G  T  K

2001  AACGAAGGGTGTTCATCATTGAGACGATGGGAGGATATTGTGGCTATCTC
        R  R  V  F  I  I  E  T  M  G  G  Y  C  G  Y  L

GCGACACTTTCTGCCCTCGCCTCTGGAGCTGATAATGCTTACATTTTCGA  2100
                  A  T  L  S  A  L  A  S  G  A  D  N  A  Y  I  F  E

2101 GGAGAAGTTCACCGTGGAGATATCATTGAGACGTGGAAGTCATCGCTGCA
       E  K  F  T  V  E  I  S  L  R  R  G  S  H  R  C  K

AAATGGCTCAAGGAGTTCAGCGATATTTGATTGTACGAAATGAGTATGCT  2200
                    M  A  Q  G  V  Q  R  Y  L  I  V  R  N  E  Y  A
```

-continued

```
2201 AACAAGAACTTTACAACGGAATTCGTAAAGCAGCTGTTCGCTGAAGAAGG
      N  K  N  F  T  T  E  F  V  K  Q  L  F  A  E  E  G

CAAAGGCGAGTTCTCAACTCGTATCAACATCCTTGGTCATGCTCAACAAG 2300
            K  G  E  F  S  T  R  I  N  I  L  G  H  A  Q  Q  G

2301 GTGGTAGCCCGACACCATTCGATCGTAACATGGGTACGAAGTTAGCTGCA
      G  S  P  T  P  F  D  R  N  M  G  T  K  L  A  A

AGAGCTTTGGAGTACATTACACAAATTAAGGAATCAATGGTTAATGG 2400
            R  A  L  E  Y  I  T  Q  I  K  E  S  M  V  N  G

2401 TGTCGTTTCTACAAAATCTCCCGAACGGGCTACCCTTCTTGGCTTGACTG
      V  V  S  T  K  S  P  E  R  A  T  L  L  G  L  T  G

GAAGACGTGTGGTGTTCACACCAGTAGAGGAATTGGCCGCTGAAACTGAC 2500
            R  R  V  V  F  T  P  V  E  E  L  A  A  E  T  D

2501 TTCGACAAACGTTTGCCTTGTGACCAGTGGTGGCTGAAGCTGCGACCGTT
      F  D  K  R  L  P  C  D  Q  W  W  L  K  L  R  P  L

ACTTCGTATTCTCGCTAAACATACTTCAATCTATCATACAGAAGCTATGG 2600
            L  R  I  L  A  K  H  T  S  I  Y  H  T  E  A  M  E

2601 AGGATACAGAGGATTACGATTAGGCCCCGTGTAAATTGAATATAGATGTT
      D  T  E  D  Y  D

CTATTATCGTCACAGTATGAGAGTAGTTGATTTCCGTCAAAGGAAAGAAT 2700

2701 CGTCGATCCTAGTGGTGTCAACTGTTGTAGTTGCGTAATAATAAA 2745
```

We claim:

1. A method of identifying compounds useful as antiparasitic drugs comprising the steps of:
   a) exposing a test group of a target gene-complemented microorganism growing in selection medium to a compound;
   b) exposing to said compound a control group of a target gene-complemented microorganism growing in selection media supplemented with permissive substrate; and
   c) comparing viability of said test group after exposure to said compound to viability of said control group after exposure to said compound;
   wherein said target gene-complemented microorganism is complemented with a gene from a helminthic parasite.

2. A method according to claim 1 further comprising the steps of:
   a) exposing a microorganism complemented with a helminthic parasite-host gene to said compound, said microorganism complemented with a helminthic parasite-host gene growing in selection media; and
   b) comparing viability of said microorganism complemented with a helminthic parasite-host gene after exposure to said compound to viability of said test group after exposure to said compound and viability of said control group after exposure to said compound;
   wherein said microorganism complemented with a helminthic parasite-host gene is complemented with a gene from a host of said helminthic parasite.

3. A recombinant DNA molecule encoding a *Haemonchus contortus* protein, selected from the group consisting of:
   phosphofructokinase and phosphoenolpyruvate carboxykinase.

4. A recombinant DNA molecule according to claim 3 wherein said protein is phosphofructokinase.

5. An expression vector comprising a recombinant DNA molecule according to claim 4.

6. A transformed host cell comprising an expression vector according to claim 5.

7. A transformed host cell according to claim 6 wherein said transformed host cell is *E. coli*.

8. A transformed host cell according to claim 7 wherein said transformed host cell is unable to produce *E. coli* phosphofructokinase.

9. A recombinant DNA molecule according to claim 3 wherein said protein is phosphoenolpyruvate carboxykinase.

10. An expression vector comprising a recombinant DNA molecule according to claim 9.

11. A transformed host cell comprising an expression vector according to claim 10.

12. A transformed host cell according to claim 11 wherein said transformed host cell is *E. coli*.

13. A transformed host cell according to claim 12 wherein said transformed host cell is unable to produce *E. coli* phosphoenolpyruvate carboxykinase.

14. A method according to claim 1 for identifying compounds useful as antinematode drugs.

15. A method according to claim 14 wherein said target gene-complemented microorganism is *E. coli* unable to produce *E. coli* phosphofructokinase and complemented with *Haemonchus contortus phosphofructokinase gene*.

16. A method according to claim 15 wherein said selection medium is mannose only.

17. A method according to claim 15 wherein said permissive substrate is glycerol only.

18. A method according to claim 14 wherein said target gene-complemented microorganism is *E. coli* unable to produce *E. coli* phosphoenolpyruvate carboxykinase and complemented with *Haemonchus contortus* phosphoenolpyruvate carboxykinase gene.

19. A method according to claim 18 wherein said selection medium is oxaloacetate only.

20. A method according to claim 18 wherein said permissive substrate is pyruvate only.

* * * * *